(12) United States Patent
Byatt et al.

(10) Patent No.: US 6,407,383 B1
(45) Date of Patent: Jun. 18, 2002

(54) METHOD AND DEVICE FOR DETERMINING THE OIL CONCENTRATION IN LIQUIDS BY MEANS OF FLUORESCENCE EXCITATION WITH AN EXCIMER LAMP

(75) Inventors: John Byatt, Klingnau; Thomas Kleiner, Kirchdorf; Ulrich Kogelschatz, Hausen; Daniel Matter, Brugg, all of (CH)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 09/294,383

(22) Filed: Apr. 20, 1999

(30) Foreign Application Priority Data

Apr. 23, 1998 (DE) ........................... 198 18 192

(51) Int. Cl.$^7$ ............................................. G01N 21/64
(52) U.S. Cl. ..................................... 250/301; 250/458.1
(58) Field of Search ............................. 250/301, 458.1, 250/459.1, 461.1

(56) References Cited

U.S. PATENT DOCUMENTS

| 2,295,366 A | 9/1942 | Stout |
| 3,581,085 A | 5/1971 | Barrett |
| 3,842,270 A | 10/1974 | Gregory et al. |
| 3,917,945 A | 11/1975 | Sema et al. |
| 4,057,721 A | 11/1977 | deVial et al. |
| 5,381,002 A | 1/1995 | Morrow et al. |
| 5,489,977 A | 2/1996 | Winslow et al. |
| 5,974,860 A * | 11/1999 | Kuroda et al. ............... 250/301 |

FOREIGN PATENT DOCUMENTS

| DE | 3020168 A1 | 12/1981 |
| DE | 3832906 A1 | 4/1989 |
| DE | 3938142 C2 | 5/1991 |
| DE | 4305704 A1 | 9/1994 |
| DE | 19507119 C2 | 9/1995 |
| DE | 19617106 A1 | 10/1997 |
| EP | 0026093 | 4/1981 |
| GB | 1489056 | 10/1977 |
| GB | 2078941 | 1/1982 |
| GB | 2273355 | 6/1994 |
| WO | 93/25891 | 12/1993 |

OTHER PUBLICATIONS

"A fluorescence trace detector for on–line contamination monitoring", Cowlin, et al., Journal of Scientific Instruments, 1968, pp. 815–816.
"Acoustically resonant pulsed photoacoutstic technique for liquids", Efthimiades, et al. Applied Optics, vol. 24, No. 15, Aug. 1985, pp. 2450–2455.
"Application of photoacoustic spectrometry to flow–injection analysis", Carrer, et al., Analytica Chimica Acta, 1995, pp. 20–27.
Sigrist Process–Photometer Technical Printout. (May 1994).
"Neue UV–Strahler fur industrielle Anwendungen", Eliasson, et al., ABB Infocom article. (Mar. 1991).

* cited by examiner

Primary Examiner—Georgia Epps
Assistant Examiner—Richard Hanig
(74) Attorney, Agent, or Firm—Burns, Doane, Swecker & Mathis, L.L.P.

(57) ABSTRACT

The present invention relates to a method and a device for fluorescence measurement of oil residues in water. The core of the invention is to use a powerful, narrow-band excimer lamp to excite intensive fluorescence radiation to detect the latter with a photodiode or the like, and to determine the oil concentration therefrom. The excimer lamp can be designed as a flat radiator a hollow cylindrical inner radiator or a tubular radiator, and can be combined with a through-flow or free fall measuring cell. The excimer lamp is advantageously operated in a pulsed or modulated fashion, the fluorescence radiation is measured at a right angle to the exciting radiation, the emitted and/or transmitted exciting light is monitored with the detectors, and a redundant measuring arrangement with a plurality of excimer lamps and fluorescence detectors is provided. The sensor is distinguished by reliability, freedom from maintenance and a long service life.

21 Claims, 7 Drawing Sheets

METHOD AND DEVICE FOR DETERMINING THE OIL CONCENTRATION IN LIQUIDS BY MEANS OF FLUORESCENCE EXCITATION WITH AN EXCIMER LAMP

BACKGROUND OF THE INVENTION

1. Field of the Invention

The invention relates to the field of fluorescence spectroscopy for detecting contaminants in liquid media, and more specifically to a method and a device for measuring the concentration of oil in water.

2. Background of the Invention

In the offshore production of oil, use is made of so-called separation tanks in which the various phases (sand, water, oil and gas) occurring during drilling are separated on the basis of their differences in density and removed in separate conduit systems. In this process, it is possible even for small amounts of oil contaminants in the waste water to lead to intolerable environmental stresses with the corresponding consequences in cost. Typical limiting values on the concentration of oil and water are 40 ppm in the case of direct disposal into the sea, and 100 ppm–5000 ppm in the case of reuse as process water, for example in the case of pumping back into the oil source. In addition, monitoring the concentration of oil in the process water supplies important information on the course of the separation, and serves for monitoring the injection process. This requires oil residue detectors which are sensitive and reliable.

High-pressure separation tanks which are suitable for operation on the sea bed 100 m or more below the surface of the sea have recently been developed. The oil produced and already separated can then be pumped to the surface of the sea with far less expenditure of energy. Such separator tanks are exposed to very high pressures of 60–180 bars, specifically the water pressure at the sea bed from outside, and the pressure of the oil produced on the inside, and to high temperatures of 50–120° C. Previously, commercially available detectors cannot be used under these difficult operating conditions. In addition, it is necessary to ensure the oil residue detector can function for years and without maintenance, since an operational failure and premature replacement would entail high costs.

U.S. Pat. No. 5,381,002 presents a fluorescence method for measuring low concentrations of dispersed oil in water. The fluorescence is based on the absorption and frequency-shifted reemission of electromagnetic radiation by aromatic hydrocarbons. The dispersion and solution of the oil in water is improved, inter alia, by mechanical measures such as, for example, by a static mixer, ultrasound or microwaves. UV light sources with exciting wavelengths in the region of 200 nm–400 nm are used, and the fluorescence is detected in the region of 250 nm 600 nm. The fluorescent intensity can be calibrated by means of a reference absorption measurement ("turbidity meter") at the emission wavelength. Non-contaminating free fall measuring cells are also proposed in addition to through-flow measuring cells.

The Sigrist-Photometer AG company markets an oil trace measuring unit which is based on fluorescence excitation by a high-pressure mercury (Hg) vapor lamp. The fluorescent light is detected at 900 to the exciting beam, in order to minimize direct scattered light from the Hg vapor lamp. Measurement is performed by comparison with a reference beam which has a fluorescence standard with a variable light attenuator and is fed through the same Hg vapor lamp. The result overall is an expensive measuring apparatus with a flicker mirror and, possibly, chopper wheel.

It is disadvantageous in the named systems that UV light sources are broadband ones which are of low efficiency, require to be maintained and are relatively short lived. Because of the low fluorescence yield, sensitive photomultipliers are mostly required as detectors. The maintenance interval of an Hg vapor lamp is typically one month, and this calls into question the usefulness of the freedom of other components, in particular a free fall measuring cell, from maintenance. Pulsed operation for the purpose of prolonging the service life is difficult to achieve.

DE 43 05 704 A1 discloses excimer lamps as UV radiation sources for ionizing particles in a gas stream. Excimer lamps supply narrow-band UV radiation by means of a quiet discharge, induced by an E field, in special filling gases. They are distinguished by high stability and long service life, high efficiency and a good degree of suitability for pulsed operation. Consideration is given as filling gases to, for example, inert gases, possibly mixed with metal vapors or halogens and, as the case may be, with a buffer gas, mercury or compounds of such elements. Excimer lamps can be implemented in multifarious forms, for example as flat radiators or as concentric inner or outer radiators.

A description of the design and mode of operation of such UV excimer radiators is also given, inter alia, in the company publication of the applicant "Neue UV-Strahler fur industrielle Anwendungen" ("New UV radiators for industrial applications"), printed publication CH-E 3.30833.0 D, which is an offprint from the company journal "ABB Technik" 3/91, pages 21–28.

SUMMARY OF THE INVENTION

Accordingly, one object of the invention is to provide an improved fluorescence measuring method for determining the concentration of oil in water, and an improved fluorescence sensor, the method and device being distinguished by simplicity, high exciting efficiency and good long term reliability.

The core of the invention is, specifically, to guide an oil-water mixture through a measuring cell, to use an excimer lamp there to excite fluorescence, to measure an intensity of the fluorescence radiation, and to determine an oil concentration therefrom.

A first exemplary embodiment exhibits a fluorescence measurement with at least one UV excimer flat radiator or tubular radiator, in which measurement fluorescent light is preferably detected at a right angle to the exciting beam and, if appropriate, the excimer power and its attenuation in the measuring cell are monitored.

A second exemplary embodiment represents a modified measuring cell with a concentric UV excimer radiator and, preferably, axially arranged detectors.

Further exemplary embodiments relate to parallel arrangements of an UV excimer tubular radiator and a tubular through-flow cell, an elliptic reflector arrangement and/or a quartz block, resistant to high pressures, for such a configuration, a free fall measuring cell and an installation of an excimer lamp fluorescence sensor for measuring the concentration of oil in water in a high-pressure separator tank.

An important advantage of the fluorescence measurement with excimer lamps includes that, because of the narrow-band, strong excimer radiation, it is possible to implement efficient fluorescence excitation and a high level of detection for dissolved and undissolved oil residues in water, even with photodiodes.

Another advantage includes that the geometry of the excimer lamp can be adapted to the shape of the measuring cell, in order to achieve efficient fluorescence excitation in a large volume, and in order to equip measuring cells with a plurality of redundant excimer radiators.

Further advantages in the use of excimer lamps are their reliability, freedom from maintenance and long service life, particularly in the case of pulsed operation. As a result, it is possible for the first time to implement in-situ fluorescence measurements which are stable in the long term even at locations which are difficult to access.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein, in cross section.

DESCRIPTION OF THE PREFERRED EMBODIMENTS

Referring now to the drawings, wherein like reference numerals designate identical or corresponding parts throughout the several views, the subject matter of the invention is a method for measuring the concentration of oil in water, in which method an oil-water mixture 7 is guided through a measuring cell 6, 23, excited there to fluorescence by an excimer lamp 2; 2a, 2b; 2c; 2d, an intensity of the fluorescence radiation 27b is measured, and an oil concentration is determined therefrom. It is preferred to use an excimer lamp 2; 2a, 2b; 2c; 2d whose filling includes xenon (Xe) with chlorine (Cl12), hydrochloric acid (HCl) or a chlorine-containing gas, to operate the excimer lamp 2; 2a, 2b; 2c; 2d in a pulsed fashion, and to measure the intensity of the fluorescence radiation 27b with photodiodes 10, 10a, 10b. The excimer lamp is advantageously constructed as a flat radiator 2; 2a, 2b, concentric inner radiator 2c or tubular radiator 2d, and the fluorescence radiation 27b is measured at a preferably right angle to the exciting radiation 27a. In particular, a quartz block 40 is provided for holding the excimer lamp 2; 2a, 2b; 2c; 2d and the measuring cell 6, 23. It is also possible to monitor the emitted and/or transmitted exciting light 27a, and to provide a redundant measuring arrangement (see FIG. 2) with at least two excimer lamps 2a, 2b and at least two fluorescence detectors 10a, 10b. Instead of a throughflow measuring cell 6, it is also possible to use a free fall measuring cell 23 (see FIG. 6) and to carry out the fluorescence measurement on a separator tank 28 (see FIG. 8), in particular a high-pressure separator tank 28. The oil in the water can be uniformly dispersed with a static mixer or the like upstream of the measuring cell 6, 23.

A redundant concentration measurement using a photo-acoustic measuring method as is known, for example, from a German patent application (file reference 197 44 500.4) of the applicant (which is not a prior publication) can be carried out to supplement the fluorescence measurement. The photo-acoustic sensor principle is based on converting optical energy into acoustic energy by the absorption on light on oil molecules in water. Photo-acoustic free fall measuring cells are described in which light is launched in a contactless fashion into the oil-water mixture, and the sound is detected with a piezoelectric pickup mounted at the outside or an optical interferometer which measures oscillations of the liquid surface in a contactless fashion. For further details, reference may be made to said patent application, the contents of which are hereby deemed to be a constituent of the present application.

Finally, it is also desirable for an additional level measurement to be carried out on a separator tank 28 and for it to be used—in addition to the measurement of oil concentration according to the invention by fluorescence measurement—to assess the separation quality in the separator tank 28. Reference may be made to the German patent applications (file references 197 57 190.5 and 197 22 837.2) of the applicant (which are not prior publications) with regard to possible measurement principles for determining levels. For example, it is possible to infer an efficient separation from a high water level and a low oil-in-water concentration, but an incomplete separation and, possibly, instances of turbulence in the separator tank 28 or similar disturbances from a high water level and a high oil-in-water concentration.

The invention also has as subject matter a fluorescence sensor 1 for measuring the concentration of oil in water. The fluorescence sensor 1 includes a measuring cell 6, 23 with an excimer lamp 2; 2a, 2b; 2c; 2d as exciting light source, and a fluorescence detector 10, 10a, 10b, which supplies an electric signal as a function of the optical fluorescent power or fluorescent intensity.

Figure 1A:
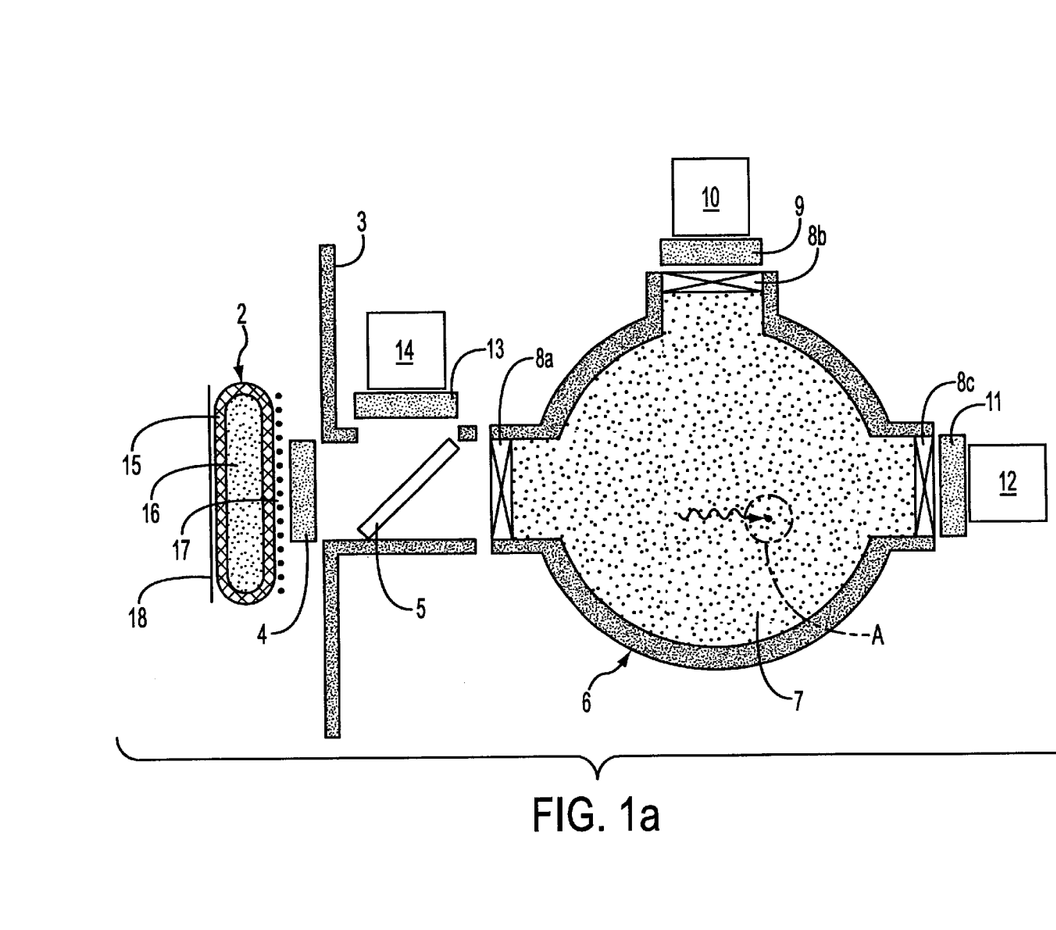
FIG. 1a illustrates a first fluorescence sensor according to the invention, with a flat UV excimer radiator.

A tubular through-flow measuring cell 6 with an excimer flat radiator 2 is represented in FIG. 1a as a first exemplary embodiment. The excimer lamp 2 is arranged, for example, in front of an optical entrance window 8a of the measuring cell 6 in a housing 3 which is pressure-proof, possibly resistant to high pressure. An exit window 8b and a detector 10 for the fluorescence radiation 27b are located at a preferably right angle. The fluorescence detector 10 is typically protected by a long-pass filter 9 from scattered excimer exciting light. It is advantageous to provide a third optical window 8c with a transmission detector 12 opposite the entrance window 8a. In addition, a beam splitter 5 with a reference detector 14 for monitoring the emitted excimer power can be inserted in front of the entrance window 8a. Bandpass filters 4, 11, 13 for the exciting light 27a are preferably located behind the excimer lamp 2 and in front of the detectors 12, 14. The optical windows 8a, 8b, 8c can be implemented in a simple way by virtue of the fact that the measuring cell 6 includes a silica glass tube 6 which is sheathed in an opaque fashion except in the region of the windows 8a, 8b, 8c. In particular, the silica glass tube 6 can have a reflecting, nonfluorescent coating for the exciting light 27a and/or the fluorescence radiation 27b.

Figure 1B:
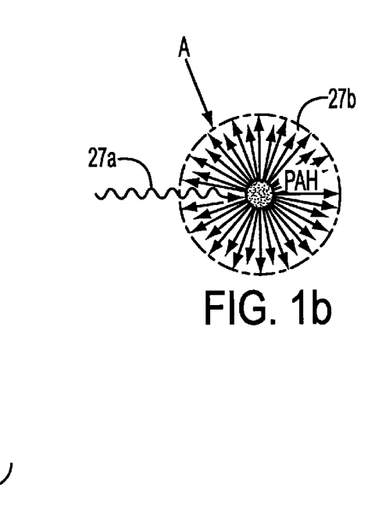
FIG. 1b illustrates a portion A of FIG. 1a at an enlarged scale.

The excimer lamp 2 is described with regard to design, mode of operation, typical filling gases and wavelengths in German laid-open application DE 43 05 701 A1, the entire contents of which are incorporated by reference herein. In principle, the excimer lamp 2 includes a closed silica glass 15 with a gas mixture 16, forming excimers under discharge conditions, an inner transparent electrode 17 and an outer reflecting electrode 18. High voltage between the electrodes 17, 18 generates quiet electric discharges in the filling gas, excites gas atoms by electron collision, forms excimers and emits UV light 27a when the latter decay.

The excimer lamp is preferably filled with xenon (Xe) and chlorine (Cl2), hydrochloric acid (HCL) or a chlorine-containing gas, and has an excimer emission at 308 nm which is concentrated on a few nm. At this wavelength, an efficient fluorescence excitation of oil, in particular of polyaromatic hydrocarbons, is possible, and at the same time the absorption in water is low. It is favorable to select a cut-off wavelength of approximately 370 nm for the long-pass filter 9, and interference filters as bandpass filters 4, 11, 13. A much more intensive fluorescence radiation 27b can be generated with narrow-band excimer lamps 2, 2a, 2b, 2c than with broadband, bandpass-filtered Hg high-pressure vapor lamps. Moreover, the spectral separation of the fluorescence radiation 27b by the long-pass filter 9 is simpler, because the excimer emission is negligibly small above 370 nm.

A decisive advantage of excimer radiators 2, 2a, 2b, 2c for fluorescence excitation is that the fluorescence radiation 27b of contaminants in the ppm region can also be measured with photodiodes 10, 10a, 10b. It is thereby possible for all the detectors 10, 10a, 10b; 12, 12a, 12b; 14, 14a, 14b to be photodiodes. The geometrical shape of the excimer lamps 2; 2a, 2b; 2c; 2d can be adapted to the measuring cell in a way resulting in a large-volume and/or highly concentrated fluorescence excitation. In particular, the reflecting electrode 18 can be shaped such that the excimer radiation 27a is concentrated in a desired way. It is also possible for the silica glass 15 to be optimized from outside with regard to thickness and shape for high-pressure loads. Finally, the typical preheating times for Hg high-pressure vapor lamps are eliminated in the case of excimer lamps 2; 2a, 2b; 2c; 2d. Consequently, the excimer lamp 2; 2a, 2b; 2c; 2d can be operated in a pulsed or modulated fashion, or be switched off between measurements. The service life can be substantially prolonged thereby. If necessary, the excimer lamp 2; 2a, 2b; 2c; 2d can, in addition, be operated with water cooling.

A further advantage of the through-flow measuring cell 6 in accordance with FIG. 1a is that it is possible to measure and correct variations in the intensity of the fluorescence radiation 27b owing to variable excimer power and/or to variable absorption or turbidity of the oil-water mixture 7. This also results in the correction of measuring errors owing to any contamination of the entrance window 8a and equally strong contamination of the windows 8b, 8c. The result is measurement of the oil concentration which is very reliable and stable in the long term.

Oil concentrations between a few ppm and approximately 500 ppm were measured with such a fluorescence sensor 1. Without transmission correction, the functional relationship between the fluorescence intensity and the oil concentration is proportional up to approximately 100 ppm, and less than proportional thereabove. This saturation effect is caused, inter alia, by the increasing turbidity of the oil-water mixture 7. With the transmission correction, the linear measuring range can be extended far beyond 500 ppm, and a possible sublinear measuring range can be realized up to even higher oil concentrations of approximately 5000 ppm.

A problem in fluorescence measurement is that the fluorescence strength decreases with transition from dissolved, via finely dispersed oil, to coarsely dispersed oil. This effect contributes to the abovementioned saturation. A stable size distribution of the dispersed oil droplets is advantageously ensured by virtue of the fact that a static mixer in front of the measuring cell 6 causes turbulence in the oil-water mixture 7, and the flow rate, the temperature and the pressure are kept constant.

For the purpose of operating the through-flow measuring cell in a fashion free from maintenance, it is desirable, in addition, to keep the contamination of the optical windows low. This can be achieved, for example, by means of an oil-repelling coating, a window cleaning device, for example using ultrasound, or by means of causing turbulence in the flow in the measuring cell.

Figure 2:
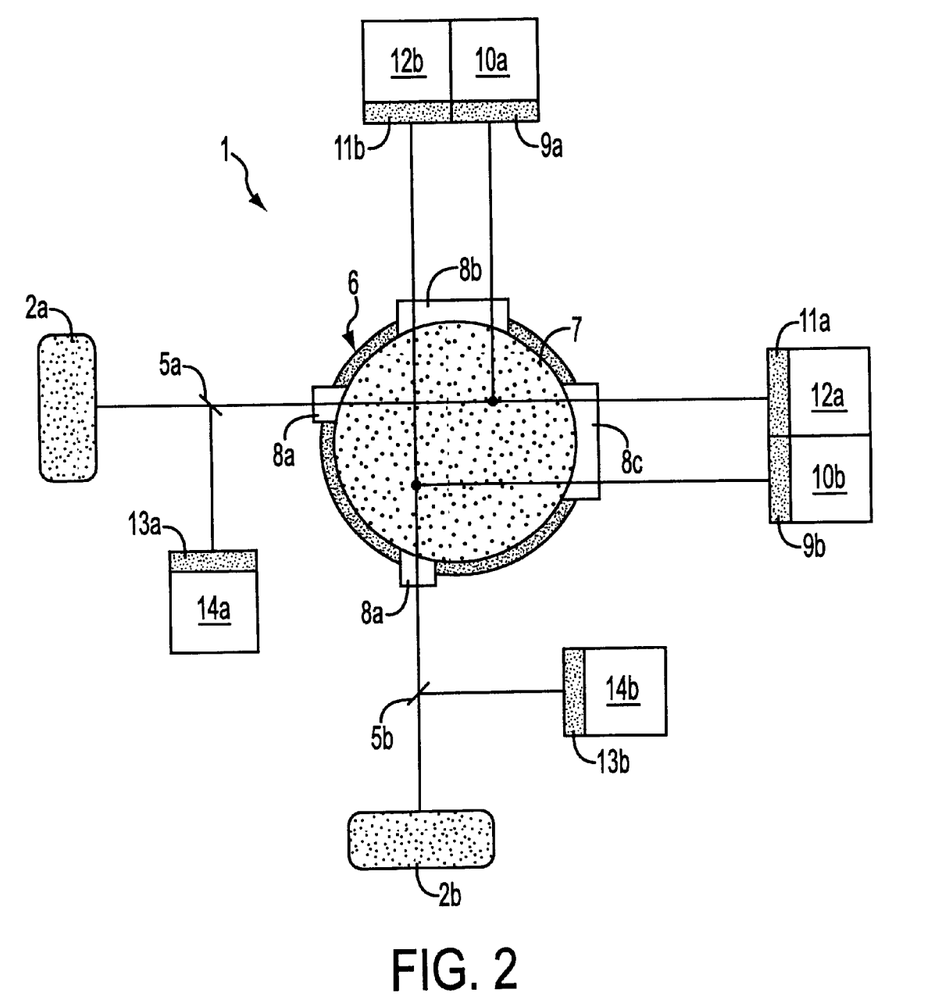
FIG. 2 illustrates a redundant arrangement with two excimer flat radiators in accordance with FIG. 1.

Another object of the invention is to create a fluorescence sensor 1 which is extremely unsusceptible to disturbance and which can also operate at inaccessible locations over long time periods. FIG. 2 shows an exemplary embodiment in which a plurality of redundant measurements can be carried out in the same measuring volume. For this purpose, at least two arrangements in accordance with FIG. 1a are provided, which include excimer lamps 2a, 2b, fluorescence detectors 10a, 10b and, optionally, transmission detectors 12a, 12b, beam splatters 5a, 5b with reference detectors 14a, 14b, long-pass filters 9a, 9b and bandpass filters 11a, 11b, 13a, 13b, and are preferably arranged at a right angle to one another. Modulation or alternating operation of the excimer lamps 2a, 2b can prevent the redundant measurements from influencing one another.

The functionality of such a redundant fluorescence sensor 1 is ensured even in the event of failure of an excimer lamp 2a, 2b or other redundant components. It is also possible to take one excimer lamp 2b into operation only once the other excimer lamp 2a has failed. It is preferable to provide a common optical window 8b for the detectors 10a, 12b, and a common optical window 8c for the detectors 10b, 12a. Falsifications of the fluorescence measurement owing to any contamination of the windows 8b and 8c can then be corrected by using the signal T12b Of the transmission detector 12b to normalize the intensity-proportional electric signal S10a, of the fluorescence detector 10a and, vice versa, by using T12a to normalize S10b- In this case, the fluorescence signals S10a and S10b are additionally normalized with respect to the optical powers of the excimer lamps 2 and 2b, respectively, that is to say to the signals L14a and L14b, respectively, at the detectors 14a and 14b, respectively, or else the optical powers L14a and L14b, respectively, are controlled to constant values.

Figure 3A:
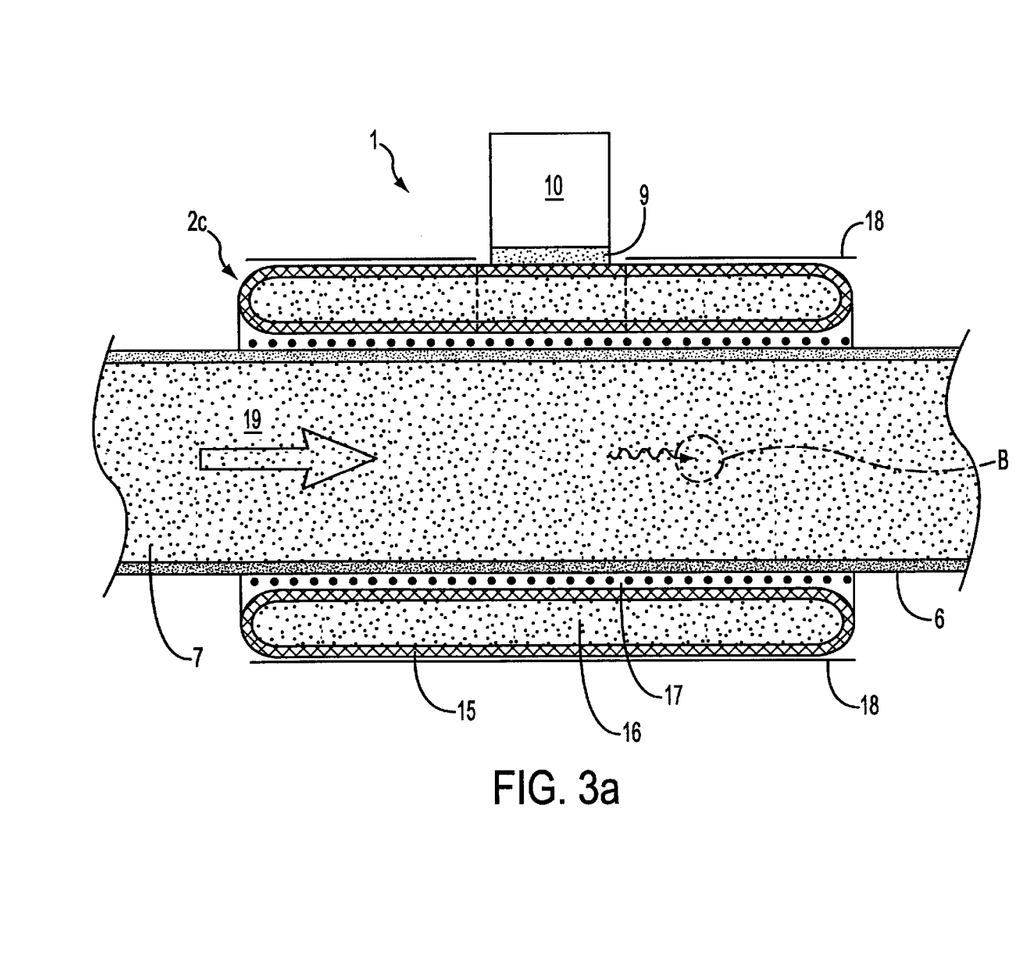
FIG. 3a illustrates a second fluorescence sensor according to the invention, with a concentric UV excimer radiator.
Figure 3B:
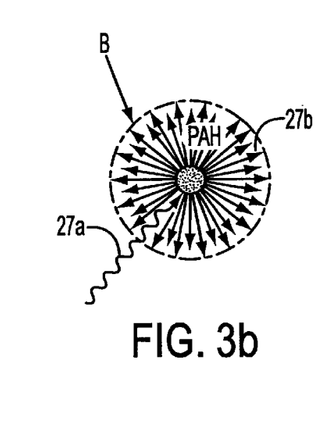
FIG. 3b illustrates a portion B of FIG. 3a at an enlarged scale.
Figure 4:
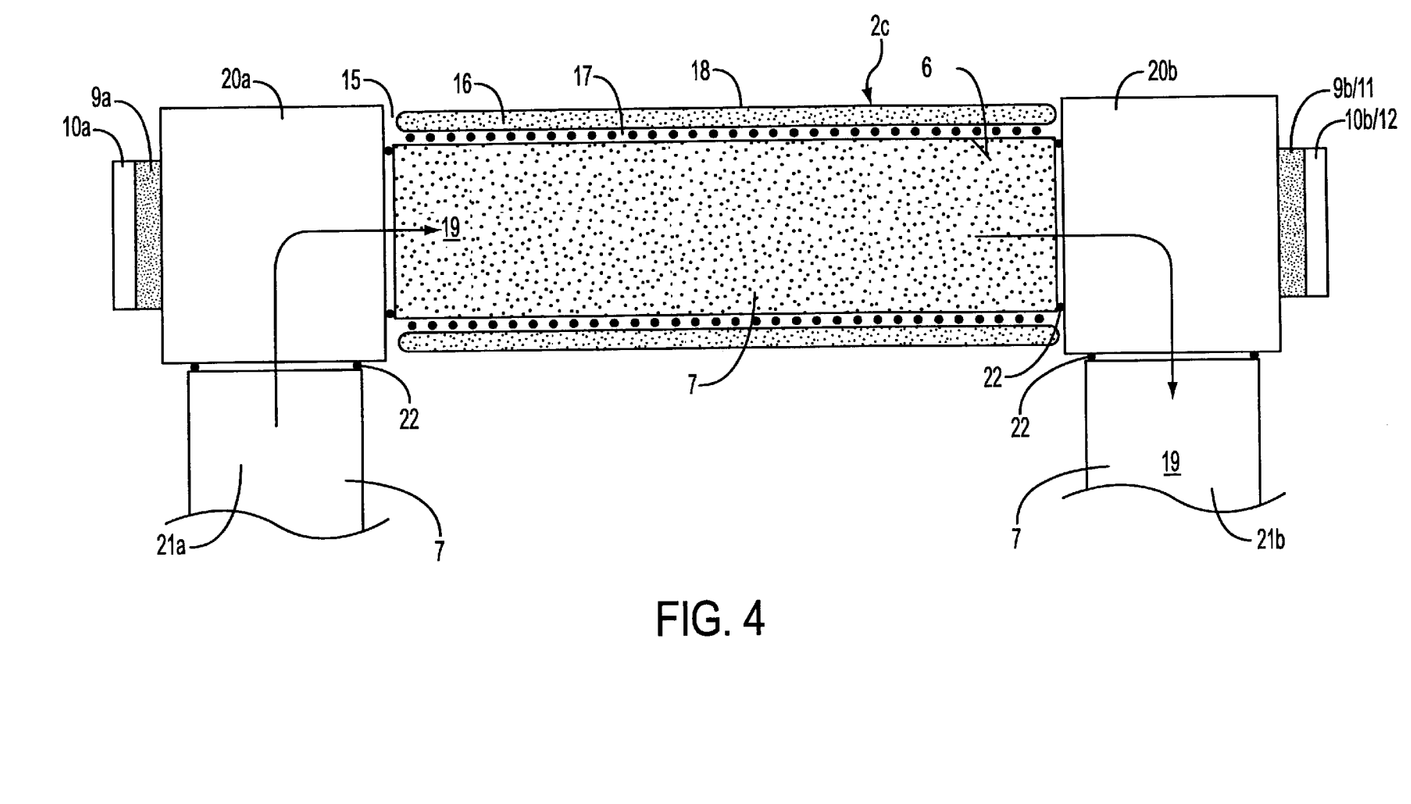
FIG. 4 illustrates a variant of FIG. 3, with axially arranged detectors.
Figure 5A:
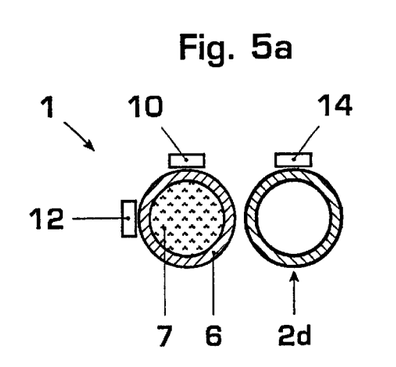
FIGS. 5a–5d illustrate a third fluorescence sensor according to the invention, with a tubular UV excimer radiator.
Figure 5B:
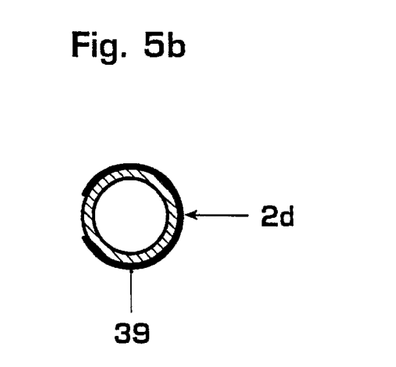
Figure 5C:
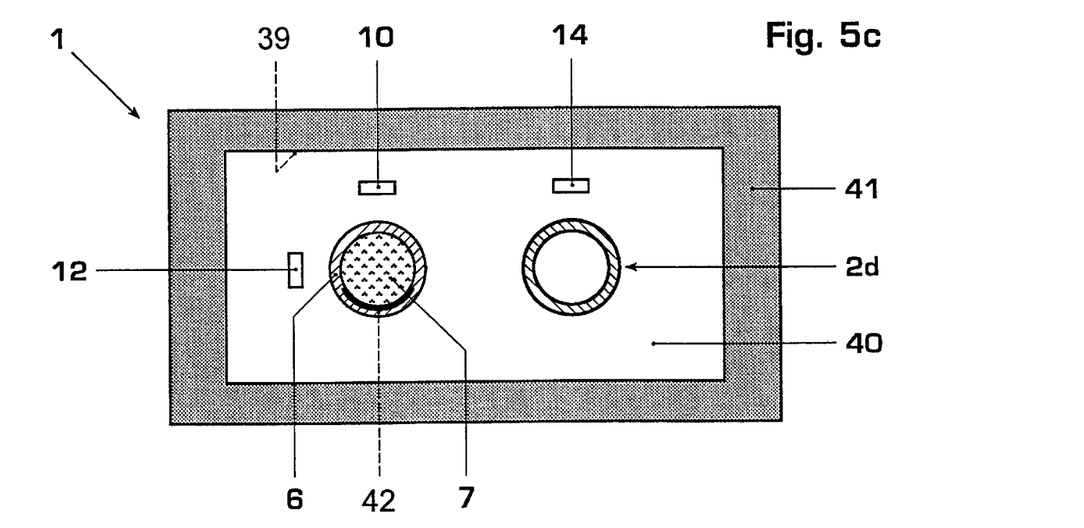
Figure 5D:
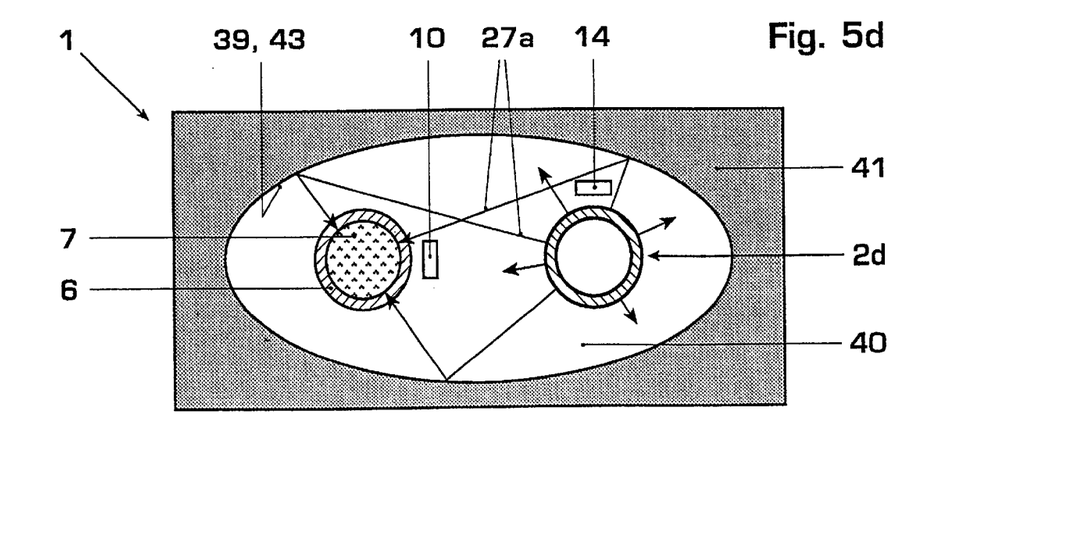

A second fluorescence sensor 1 according to the invention is represented in FIGS. 3a, 3b, and 4. The excimer lamp 2c is a hollow cylindrical inner radiator 2c which concentrically surrounds a tubular throughflow measuring cell 6 or a free fall measuring cell 23, at least one fluorescence detector (10, 10a, 10b) preferably being fitted on the axis of the excimer lamp (2c), and a transmission detector (12, 12a, 12b) being present, in particular.

In detail, FIG. 3a shows a measuring cell made from a transparent silica glass tube 6 for the oil-water mixture 7 with the through-flow direction 19. The excimer lamp 2c has, for example, an aluminum foil 18 as reflecting electrode. The exciting light 27b is thereby strongly concentrated in the measuring cell 6. A fluorescence detector 10 is mounted, for example, laterally. In order to minimize the losses in fluorescence radiation 27b upon traversing the excimer lamp 2c, the excimer lamp 2c can have a cutout (indicated by dashes). Particular preference is given to the solution of FIG. 4, where the measuring cell 6 is connected via O ring seals 22 and holders 20a, 20b to angled-off tubes 21a, 21b for guiding the oil-water mixture 7. The advantage is that it is possible to arrange the fluorescence detector 10a with a long-pass filter 9a and, optionally, a transmission detector 12 with a bandpass filter and/or a second fluorescence detector 10b with a long-pass filter 9b on the axis of the measuring cell 6. It is possible as a result to optimize the intensity both of the exciting light 27a and of the fluorescence radiation 27b.

Exemplary embodiments relating to a third fluorescence sensor 1 according to the invention are represented diagrammatically in cross section in FIG. 5. The excimer lamp 2d is advantageously a tubular radiator 2d which is arranged essentially parallel and close by a tubular through-flow measuring cell 6 or free fall measuring cell 23. The detectors 10, 14 and 12 correspond with regard to their function and arrangement to those of FIGS. 1a and 2. Because of the elongated shape of the tubular radiator 2d and of the measuring cell 6, 23, it is possible to achieve a large-volume excitation without separate windows. For the purpose of concentrating the exciting light 27a, the tubular radiator can be provided with an UV-reflecting layer 39 on the side averted from the measuring cell 6, 23. Again, for the purpose of concentrating the fluorescence radiation 27b, the measuring cell 6, 23 can be provided with an UVreflecting layer 42 on the side averted from the fluorescence detector 10. The tubular radiator 2d and the measuring cell 6, 23 are typically mounted in a housing 41. It is preferred to implement a fluorescence sensor 1 which is resistant to high pressure by constructing a quartz block 40 for holding the tubular radiator 2d and the measuring cell 6, 23 as well as at least one fluorescence detector 10 and, as the case may be, at least one transmission detector 10 and/or reference detector 14. For this purpose, appropriate bores, preferably blind bores, are provided in the quartz block 40. After the excimer lamp 2; 2a, 2b; 2c; 2d, the measuring cell(s) 6, 23 and the detectors 10, 10a, 10b; 12, 12a, 12b; 14, 14a, 14b have been inserted, the bore openings are sealed with a cover and appropriate seals. The quartz block 40 is preferably provided on the outside with an UV-reflecting layer 39 for concentrating the exciting light 27a. The quartz block 40 can be constructed as a cuboid or, in a particularly preferred fashion, as an elliptically cylindrical reflector 43 on whose focusing lines the tubular radiator 2d and the measuring cell 6, 23 are arranged. The reflector 43 is provided, for example, with a layer 39 which reflects the exciting light 27a.

The quartz block 40 is transparent to the exciting light 27a and the fluorescence radiation 27b, and simultaneously lends the sensor 1 the desired mechanical stability and resistance to high pressure. Moreover, the fluorescence sensor 1 according to FIG. 5 is distinguished in that a plurality of excimer lamps 2; 2a, 2b; 2c; 2d can be arranged one behind another in order to achieve a redundancy or a prolongation of service life, and that a plurality of light detectors 10 or 12 or 14 can be arranged one behind another in order to achieve a redundancy or an improvement in measuring accuracy by means of averaging.

Figure 6:
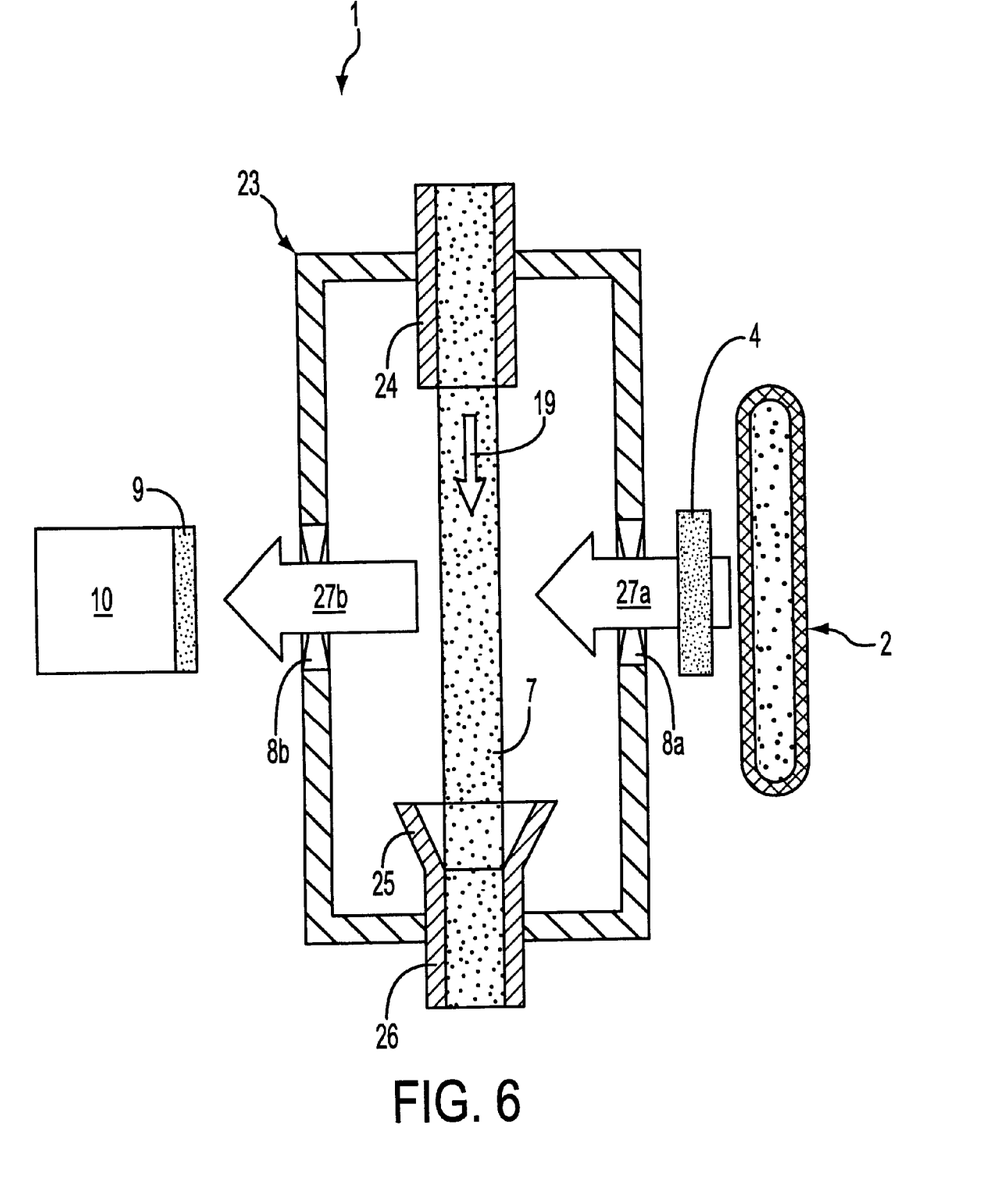
FIG. 6 illustrates a freefall measuring cell for a fluorescence sensor in accordance with FIGS. 1–5d.

FIG. 6 shows a diagram of a free fall measuring cell 23 which can be used instead of the through-flow measuring cell 6 previously discussed. The oil-water mixture 7 flows through an inlet 24 in the direction 19, forms a free-falling jet, is collected by a funnel 25 and led off via a discharge tube 26. optical windows 8a and 8b for the exciting light 27a and the fluorescence radiation 27b are provided at the level of the free-fall jet. The windows 8b, 8c are preferably arranged at a right angle to one another. It is also possible to provide a protective gas in order to prevent contamination of the optical windows 8a, 8b, 8c, etc. The protective gas can be captured in a stationary state in the free fall cell 1a, or circulate via feed lines and discharge lines. In particular, instead of air, nitrogen or argon, for example, it is also possible to use the natural gas occurring during oil production as the protective gas. Such a free fall cell can be used with all the fluorescence sensors 1 represented above.

Figure 7:
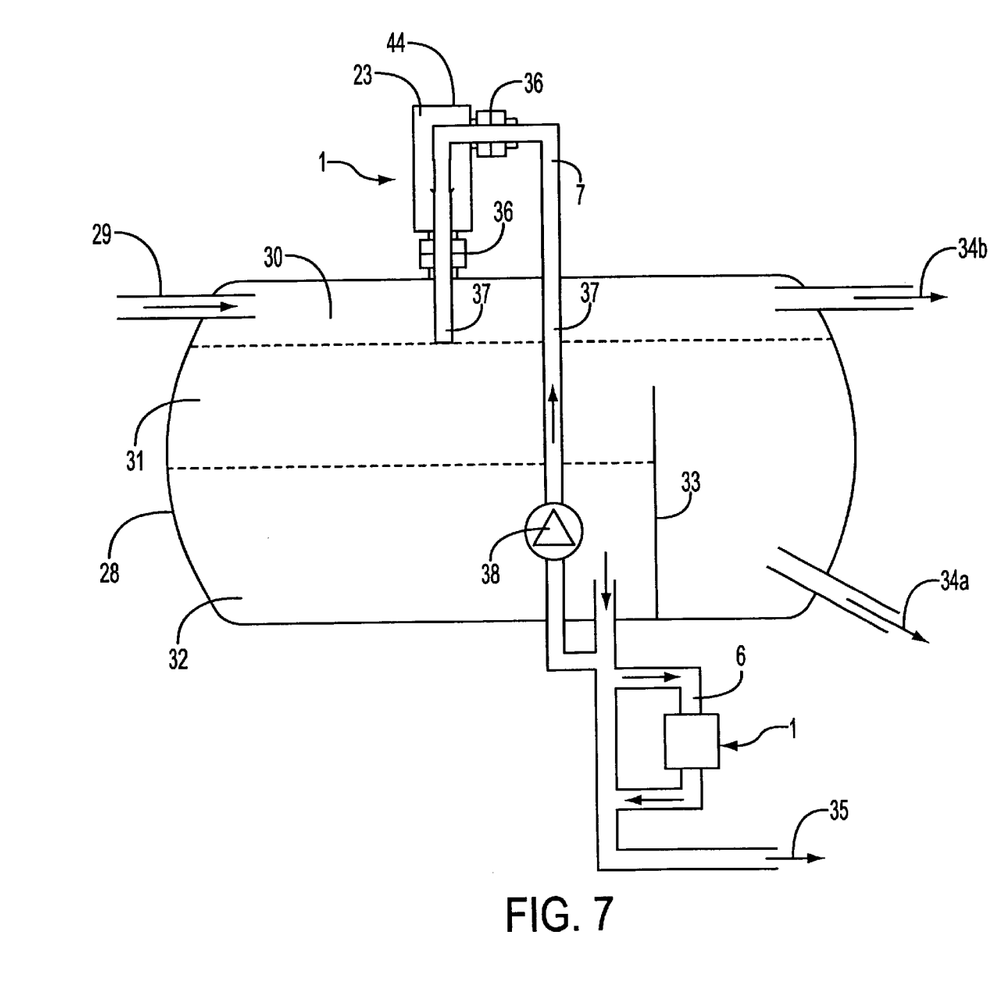
FIG. 7 illustrates an installation of an excimer fluorescence sensor in a high-pressure separator tank.

A through-flow measuring cell 6 and/or a free fall cell 23 mounted according to the invention on a high-pressure separator tank 28 are to be seen in FIG. 7. The tank 28 is filled via an inlet 29. The phases of gas 30, oil 31 and water 32 are separated by sedimentation. The oil 31 is drained through an outlet 34a, the water 32 through an outlet 35, and the gas 30 through an outlet 34b. The through-flow measuring cell 6 is located in the water outlet 35, in particular as represented in a branch provided therefor. The free fall cell 23 is located in a pressure housing 44 which is connected to the water outlet 35 and the tank 28 via connections 36 and feed lines 37. Electric supply and signaling lines are not represented. The through flow in the free fall measuring cell 23 can be controlled by a pump 38. The internal pressure of the cell 23 corresponds to the pressure in the separator tank 28. The protective gas volume in the free fall measuring cell 23 can be exchanged with the gas 30 in the tank 28 via lines which are not represented explicitly.

The problem of window soiling is further ameliorated by the free fall measuring cell 23 according to the invention. Direct contact between the optical windows 8a, 8b, 8c etc. and the oil-water mixture is avoided by the contactless optical excitation. It is possible to dispense with devices for cleaning optical windows 8a, 8b, 8c and with the windows 8a, 8b, 8c, etc. themselves.

In addition, it is possible to provide for redundancy purposes a free fall measuring cell 23 which is both a fluorescence free fall measuring cell 23 according to the invention and a photo-acoustic free fall measuring cell. The fluorescence sensor 1 is advantageously mounted on a separator tank 28 which is equipped with a level sensor.

The overall result of using excimer lamps 2; 2a, 2b; 2c; 2d for fluorescence excitation in throughflow and free fall measuring cells 6, 23 is a robust, reliable and maintenance-free sensor 1 for in-situ remote monitoring of oil in water over a large measuring range (1 ppm–5000 ppm).

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for measuring the concentration of oil in water comprising the steps of:

guiding an oil-water mixture through a measuring cell;

exciting said oil-water mixture in said measuring cell to fluorescence by an excimer lamp light source;

measuring an intensity of the fluorescence radiation; and determining an oil concentration from the radiation intensity.

2. The method for measuring the concentration of oil in water as claimed in claim 1, wherein use is made of an excimer lamp whose filling comprises xenon (Xe) with chlorine ($Cl_2$), hydrochloric acid (HCl), or a chlorine containing gas, said method comprising the further steps of:

operating the excimer lamp in a pulsed fashion, and measuring the intensity of the fluorescence radiation with photodiodes.

3. The method for measuring the concentration of oil in water as claimed in claim 2, wherein the excimer lamp is a flat radiator, a concentric inner radiator, or a tubular radiator, said method comprising the further steps of:

measuring the fluorescence radiation at a right angle to the exciting radiation, and providing a quartz block for holding the excimer lamp and the measuring cell.

4. The method for measuring the concentration of oil in water as claimed in claim 3, further comprising the steps of:

monitoring the emitted and/or transmitted exciting light, and carrying out a redundant measurement at least with two excimer lamps and two fluorescence detectors.

5. The method for measuring the concentration of oil in water as claimed in claim 4, further comprising the steps of:

using a free fall measuring cell, and carrying out the fluorescence measurement at a separator tank.

6. The method for measuring the concentration of oil in water as claimed in claim 5, further comprising the step of:

carrying out a redundant concentration measurement with a photo-acoustic measuring method;

carrying out and using an additional level measurement to assess the separation quality in the separator tank; or both.

7. The method for measuring the concentration of oil in water as claimed in claim 4, wherein said step of carrying out fluorescence measurement is carried out at a high-pressure separator tank.

8. The method for measuring the concentration of oil in water as claimed in claim 1, further comprising the steps of:

monitoring the emitted and/or transmitted exciting light, and carrying out a redundant measurement at least with two excimer lamps and two fluorescence detectors.

9. A fluorescence sensor for measuring the concentration of oil in water comprising:

an exciting light source;

a measuring cell; and a fluorescence detector;

wherein the exciting light source is an excimer lamp.

10. The fluorescence sensor as claimed in claim 9, further comprising:

at least two optical windows, and wherein the excimer lamp is a flat radiator; and the fluorescence detector is fitted at a substantially right angle to the exciting radiation.

11. The fluorescence sensor as claimed in claim 9, wherein the excimer lamp comprises a hollow cylindrical inner radiator which concentrically surrounds a tubular through-flow measuring cell or a free fall measuring cell, at least one fluorescence detector is fitted substantially on an axis of the inner radiator.

12. The fluorescence sensor as claimed in claim 9, wherein the excimer lamp comprises a tubular radiator, and further comprising:

a quartz block constructed for holding the tubular radiator, a tubular through-flow measuring cell or a free fall measuring cell, and a fluorescence detector.

13. The fluorescence sensor as claimed in claim 9, further comprising:

a redundant measuring arrangement, and wherein the excimer lamp has a filling of xenon (Xe) and chlorine ($Cl_2$), hydrochloric acid (HCl), or a chlorine-containing gas, and the detectors comprise photodiodes.

14. The fluorescence sensor as claimed in claim 13, wherein the fluorescence sensor is mounted on a separator tank with a level sensor.

15. The fluorescence sensor as claimed in claim 10, further comprising:

a transmission detector and a reference detector.

16. The fluorescence sensor as claimed in claim 11, further comprising:

a transmission detector.

17. The fluorescence sensor as claimed in claim 12, wherein the quartz block comprises an elliptically cylindrical reflector on whose focal lines the tubular radiator and the measuring cell are arranged.

18. The fluorescence sensor as claimed in claim 17, wherein the quartz block is constructed for holding a transmission detector, a reference detector, or both.

19. The fluorescence sensor as claimed in claim 13, wherein the redundant measuring arrangement comprises two excimer lamps and two fluorescence detectors.

20. The fluorescence sensor as claimed in claim 19, wherein the measuring cell comprises a static mixer.

21. The fluorescence sensor as claimed in claim 14, further comprising:

a free fall measuring cell comprising a photo-acoustic free fall measuring cell.

* * * * *